United States Patent [19]

Stogryn

[11] 4,417,075
[45] Nov. 22, 1983

[54] DI-(SECONDARY AND TERTIARYALKYLAMINOALKOXY)ALKANES

[75] Inventor: Eugene L. Stogryn, Edison, N.J.

[73] Assignee: Exxon Research and Engineering Co., Florham Park, N.J.

[21] Appl. No.: 339,899

[22] Filed: Jan. 18, 1982

[51] Int. Cl.³ .................... C07C 93/04; B01D 53/54
[52] U.S. Cl. .................... 564/505; 423/223; 423/228; 423/229; 423/232; 423/234; 564/476; 564/477; 564/508
[58] Field of Search ............... 564/508, 505

[56] References Cited

U.S. PATENT DOCUMENTS

| 3,398,197 | 8/1968 | Miller, Jr. et al. | 260/584 |
| 3,449,432 | 6/1969 | Borstlap et al. | 260/584 |
| 3,478,096 | 11/1969 | Cyba | 260/563 |
| 3,962,238 | 6/1976 | Mauvernay et al. | 260/247.2 B |
| 4,112,051 | 9/1978 | Sartori et al. | 423/223 |
| 4,112,052 | 9/1978 | Sartori et al. | 423/228 |
| 4,217,236 | 8/1980 | Sartori et al. | 252/189 |

FOREIGN PATENT DOCUMENTS 2017524 10/1979 United Kingdom ............... 564/505

OTHER PUBLICATIONS

Frazier and Kohl, *Ind. and Eng. Chem.*, 42, No. 11 (1950).
N. M. Khanna, et al., *Chem. Abs.*, vol. 49, 1725d (1955).
W. Reppe, *Chem. Abs.*, vol. 50, 16782b (1956).

*Primary Examiner*—John Doll
*Attorney, Agent, or Firm*—Albert P. Halluin

[57] ABSTRACT

A novel class of di-secondary aminoethers of the general formula:

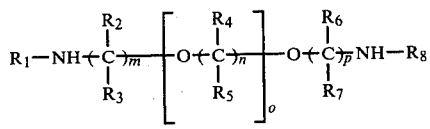

are disclosed wherein $R_1$ and $R_8$ are each independently selected from the group consisting of primary alkyl having 1 to 8 carbon atoms and primary hydroxyalkyl having 2 to 8 carbon atoms, secondary alkyl and secondary hydroxyalkyl radicals having 3 to 8 carbon atoms, tertiary alkyl and tertiary hydroxyalkyl radicals having 4 to 8 carbon atoms, $R_2$, $R_3$, $R_4$, $R_5$, $R_6$ and $R_7$ are each independently selected from the group consisting of hydrogen, $C_1$–$C_3$ alkyl and hydroxyalkyl radicals, with the proviso that $R_2$, $R_3$, $R_6$, and $R_7$ are $C_1$–$C_4$ alkyl or hydroxyalkyl radicals when $R_1$ and $R_8$ are primary alkyl or hydroxyalkyl radicals, and at least one of $R_2$ or $R_3$ and $R_6$ or $R_7$ are $C_1$ to $C_3$ alkyl or hydroxyalkyl radicals when $R_1$ and $R_8$ are secondary alkyl radicals, m, n and p are positive integers ranging from 2 to 4, and o is either zero or a positive integer ranging from 1 to 10. The compounds are useful in the selective removal of $H_2S$ from gaseous mixtures containing $H_2S$ and $CO_2$.

13 Claims, 3 Drawing Figures

Absorption-regeneration unit for selective H₂S removal

Sparged absorber unit for selective H₂S removal

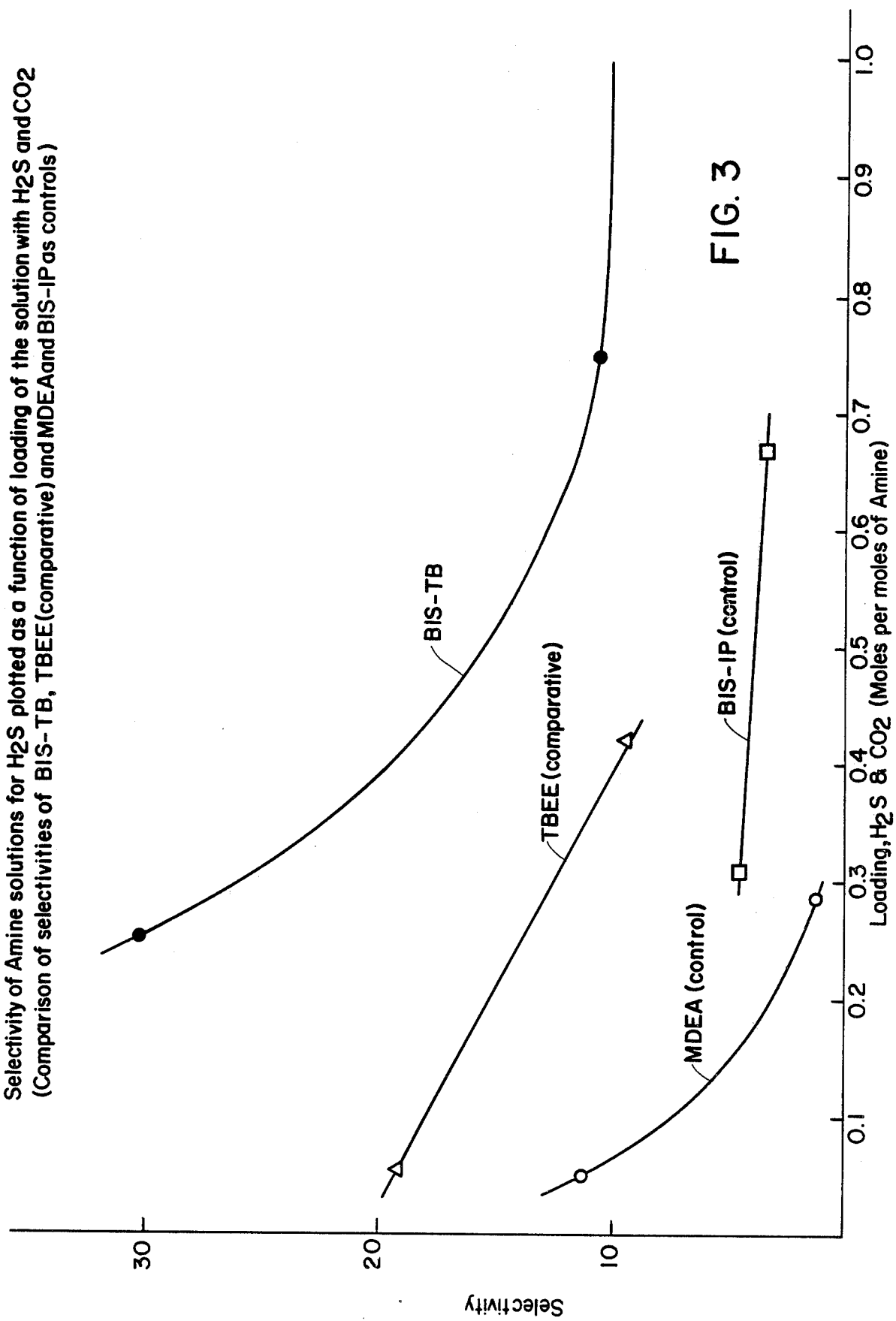

DI-(SECONDARY AND TERTIARYALKYLAMINOALKOXY)ALKANES

BACKGROUND OF THE INVENTION

1. Field of the Invention

The present invention relates to a class of di-secondary aminoethers and their preparation. These compounds are useful, for example in the removal of hydrogen sulfide from normally gaseous streams containing hydrogen sulfide including selective removal from such streams which contain hydrogen sulfide and carbon dioxide.

2. Description of Related Patents

It is well known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently.

The treatment of acid gas mixtures containing, inter alia, $CO_2$ and $H_2S$ with amine solutions typically results in the simultaneous removal of substantial amounts of both the $CO_2$ and $H_2S$. For example, in one such process generally referred to as the "aqueous amine process," relatively concentrated amine solutions are employed. A recent improvement on this process involves the use of sterically hindered amines as described in U.S. Pat. No. 4,112,052, to obtain nearly complete removal of acid gases such as $CO_2$ and $H_2S$. This type of process may be used where the partial pressures of the $CO_2$ and related gases are low. Another process often used for specialized applications where the partial pressure of $CO_2$ is extremely high and/or where many acid gases are present, e.g., $H_2S$, COS, $CH_3SH$ and $CS_2$ involves the use of an amine in combination with a physical absorbent, generally referred to as the "nonaqueous solvent process." An improvement on this process involves the use of sterically hindered amines and organic solvents as the physical absorbent such as described in U.S. Pat. No. 4,112,051.

It is often desirable, however, to treat acid gas mixtures containing both $CO_2$ and $H_2S$ so as to remove the $H_2S$ selectively from the mixture, thereby minimizing removal of the $CO_2$. Selective removal of $H_2S$ results in a relatively high $H_2S/CO_2$ ratio in the separated acid gases which simplifies the conversion of $H_2S$ to elemental sulfur using the Claus process.

The typical reactions of aqueous secondary and tertiary amines with $CO_2$ and $H_2S$ can be represented as follows:

$$H_2S + R_3N \rightleftharpoons R_3NH^+ + SH^- \quad (1)$$

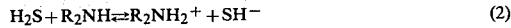

$$H_2S + R_2NH \rightleftharpoons R_2NH_2^+ + SH^- \quad (2)$$

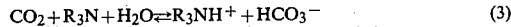

$$CO_2 + R_3N + H_2O \rightleftharpoons R_3NH^+ + HCO_3^- \quad (3)$$

$$CO_2 + 2R_2NH \rightleftharpoons R_2NH_2^+ + R_2NCOO^- \quad (4)$$

wherein R is an organic radical which may be the same or different and may be substituted with a hydroxy group. The above reactions are reversible, and the partial pressures of both $CO_2$ and $H_2S$ are thus important in determining the degree to which the above reactions occur.

While selective $H_2S$ removal is applicable to a number of gas treating operations including treatment of hydrocarbon gases from shale pyrolysis, refinery gas and natural gas having a low $H_2S/CO_2$ ratio, it is particularly desirable in the treatment of gases wherein the partial pressure of $H_2S$ is relatively low compared to that of $CO_2$ because the capacity of an amine to absorb $H_2S$ from the latter type gases is very low. Examples of gases with relatively low partial pressures of $H_2S$ include synthetic gases made by coal gasification, sulfur plant tail gas and low-Joule fuel gases encountered in refineries where heavy residual oil is being thermally converted to lower molecular weight liquids and gases.

Although it is known that solutions of primary and secondary amines such as monoethanolamine (MEA), diethanolamine (DEA), dipropanolamine (DPA), and hydroxyethoxyethylamine (DGA) absorb both $H_2S$ and $CO_2$ gas, they have not proven especially satisfactory for preferential absorption of $H_2S$ to the exclusion of $CO_2$ because the amines undergo a facile reaction with $CO_2$ to form carbamates.

Diisopropanolamine (DIPA) is relatively unique among secondary aminoalcohols in that it has been used industrially, alone or with a physical solvent such as sulfolane, for selective removal of $H_2S$ from gases containing $H_2S$ and $CO_2$, but contact times must be kept relatively short to take advantage of the faster reaction of $H_2S$ with the amine compared to the rate of $CO_2$ reaction as shown in Equations 2 and 4 hereinabove.

In 1950, Frazier and Kohl, *Ind. and Eng. Chem.*, 42, 2288 (1950) showed that the tertiary amine, methyldiethanolamine (MDEA), has a high degree of selectivity toward $H_2S$ absorption over $CO_2$. This greater selectivity was attributed to the relatively slow chemical reaction of $CO_2$ with tertiary amines as compared to the rapid chemical reaction of $H_2S$. The commercial usefulness of MDEA, however, is limited because of its restricted capacity for $H_2S$ loading and its limited ability to reduce the $H_2S$ content to the level at low pressures which is necessary for treating, for example, synthetic gases made by coal gasification.

Recently, U.K. Patent Publication No. 2,017,524A to Shell disclosed that aqueous solutions of dialkyl-monoalkanolamines, and particularly diethylmonoethanolamine (DEAE), have higher selectivity and capacity for $H_2S$ removal at higher loading levels than MDEA solutions. removal at higher loading levels than MDEA solutions. Nevertheless, even DEAE is not very effective for the low $H_2S$ loading frequently encountered in the industry. Also, DEAE has a boiling point of only 161° C., therefore it is characterized as being a low-boiling, relatively highly volatile amino alcohol. Such high volatilities under most gas scrubbing conditions result in large material losses with consequent losses in economic advantages.

SUMMARY OF THE INVENTION

It has now been discovered that absorbent solutions of a certain class of amino compounds defined as di-secondary aminoethers, and more specifically di-(secondary and tertiary alkylaminoalkoxy)alkanes, have a high selectivity for $H_2S$ compared to $CO_2$. These amino compounds surprisingly maintain their high selectivity at high $H_2S$ and $CO_2$ loadings.

By the term "severely sterically hindered" it is meant that the nitrogen atom of the amino moiety is attached to one or more bulky carbon groupings. Typically, the severely sterically hindered amino compounds of the present invention have a degree of steric hindrance such that the cumulative $-E_s$ value (Taft's steric hindrance constant) is greater than about 1.75 as calculated from the values given for primary amines in Table V from D. F. DeTar, *Journal of Organic Chemistry*, 45, 5174(1980), the entire disclosure of which is incorporated herein by reference.

The present invention relates to a specific class of bis-secondary aminoethers, and more specifically di-(secondary and tertiary alkylaminoalkoxy)alkanes of the general formula:

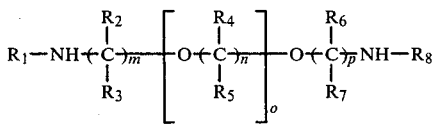

wherein $R_1$ and $R_8$ are each independently selected from the group consisting of primary alkyl having 1 to 8 carbon atoms and primary hydroxyalkyl radicals having 2 to 8 carbon atoms, secondary alkyl and secondary hydroxyalkyl having 3 to 8 carbon atoms, tertiary alkyl and tertiary hydroxyalkyl or cycloalkyl and hydroxycycloalkyl radicals having 4 to 8 carbon atoms, $R_2$, $R_3$, $R_4$, $R_5$, $R_6$ and $R_7$ are each independently selected from the group consisting of hydrogen, $C_1$-$C_4$ alkyl and hydroxyalkyl radicals, with the proviso that $R_2$, $R_3$, $R_6$ and $R_7$ bonded to the carbon atoms directly bonded to the nitrogen atoms are $C_1$-$C_4$ alkyl or hydroxyalkyl radicals when $R_1$ and $R_8$ are primary alkyl or primary hydroxyalkyl radicals, that at least one of $R_2$ or $R_3$ and $R_6$ or $R_7$ bonded directly to the carbon atoms directly bonded to the nitrogen atoms are $C_1$ to $C_4$ alkyl or hydroxyalkyl radicals when $R_1$ and $R_8$ are secondary alkyl, secondary hydroxyalkyl, cycloalkyl or hydroxycycloalkyl radicals, m, n and p are positive integers running from 2 to 4, and o is either zero or a positive integer ranging from 1 to 10. Preferably, $R_1$ and $R_8$ are selected from the group consisting of tertiarybutyl, tertiary-amyl, isopropyl, and cycloalkyl radicals, e.g., cyclopentyl and cyclohexyl radicals. Most preferably, $R_1$ and $R_8$ are both tertiary-butyl radicals and $R_2$, $R_3$, $R_4$, $R_5$, $R_6$ and $R_7$ are hydrogen. When $R_1$ and $R_8$ are secondary-alkyl radicals, it is preferred that each of $R_2$ and $R_6$ is a methyl radical; in such case $R_1$ and $R_8$ are preferably isopropyl radicals. The symbols m, n and p are preferably 2, whereas the symbol o is preferably zero or 1 or 2.

The above-identified compounds can be used in a process for the selective absorption of $H_2S$ from a normally gaseous mixture containing $H_2S$ and $CO_2$ comprising:

(a) contacting said normally gaseous mixture with an absorbent solution comprising: a bis-aminoether wherein each amino group is a severely sterically hindered secondary amine, (these bis-aminoethers typically have a p$K_a$ at 20° C. greater than 8.6 and a boiling point at 760 mm greater than 180° C. and are further characterized as capable of selectively absorbing $H_2S$ from a mixture of $H_2S$ and $CO_2$ at a "selectivity" value of at least 10 at a loading of at least 0.1 mole of $H_2S$ and $CO_2$ per moles of the amine) under conditions such that $H_2S$ is selectively absorbed from said mixture;

(b) regenerating, at least partially, said absorbent solution containing $H_2S$; and (c) recycling the regenerated solution for the selective absorption of $H_2S$ by contacting as in step (a).

Preferably, the regeneration step is carried out by heating and stripping and more preferably heating and stripping with steam.

One of the preferred amino compounds is 1,2-bis(tertiarybutylaminoethoxy)ethane.

The amino compounds herein are further characterized by their low volatility and high solubility in water at selective $H_2S$ removal conditions, and most of the compounds are also generally soluble in polar organic solvent systems which may or may not contain water. The term "absorbent solution" as used herein includes but is not limited to solutions wherein the amino compound is dissolved in a solvent selected from water or a physical absorbent or mixtures thereof. Solvents which are physical absorbents (as opposed to the amino compounds which are chemical absorbents) are described, for example, in U.S. Pat. No. 4,112,051, the entire disclosure of which is incorporated herein by reference, and include, e.g., aliphatic acid amides, N-alkylated pyrrolidones, sulfones, sulfoxides, glycols and the mono- and diethers thereof. The preferred physical absorbents herein are sulfones, and most particularly, sulfolane.

The absorbent solution ordinarily has a concentration of amino compound of about 0.1 to 6 moles per liter of the total solution, and preferably 1 to 4 moles per liter, depending primarily on the specific amino compound employed and the solvent system utilized. If the solvent system is a mixture of water and a physical absorbent, the typical effective amount of the physical absorbent employed may vary from 0.1 to 5 moles per liter of total solution, and preferably from 0.5 to 3 moles per liter, depending mainly on the type of amino compound being utilized. The dependence of the concentration of amino compound on the particular compound employed is significant because increasing the concentration of amino compound may reduce the basicity of the absorbent solution, thereby adversely affecting its selectivity for $H_2S$ removal, particularly if the amino compound has a specific aqueous solubility limit which will determine maximum concentration levels within the range given above. It is important, therefore, that the proper concentration level appropriate for each particular amino compound be maintained to insure satisfactory results.

The solution of this invention may include a variety of additives typically employed in selective gas removal processes, e.g., antifoaming agents, antioxidants, corrosion inhibitors, and the like. The amount of these additives will typically be in the range that they are effective, i.e., an effective amount.

Also, the amino compounds described herein may be admixed with other amino compounds as a blend, preferably with methyldiethanolamine. The mole ratio of the respective amino compounds may vary widely, for example, from 1 to 99 percent of the amino compounds described herein.

BRIEF DESCRIPTION OF THE DRAWINGS

FIG. 3 graphically illustrates the selectivity for H₂S plotted against the H₂S and CO₂ loading for 1,2-bis-(tertiarybutylaminoethoxy)ethane (BIS-TB) as compared to tertiarybutylaminoethoxyethanol (TBEE), 1,2-bis-(isopropylaminoethoxy)ethane (BIS-IP), and methyldiethanolamine (MDEA).

DESCRIPTION OF THE PREFERRED EMBODIMENTS

Figure 1:
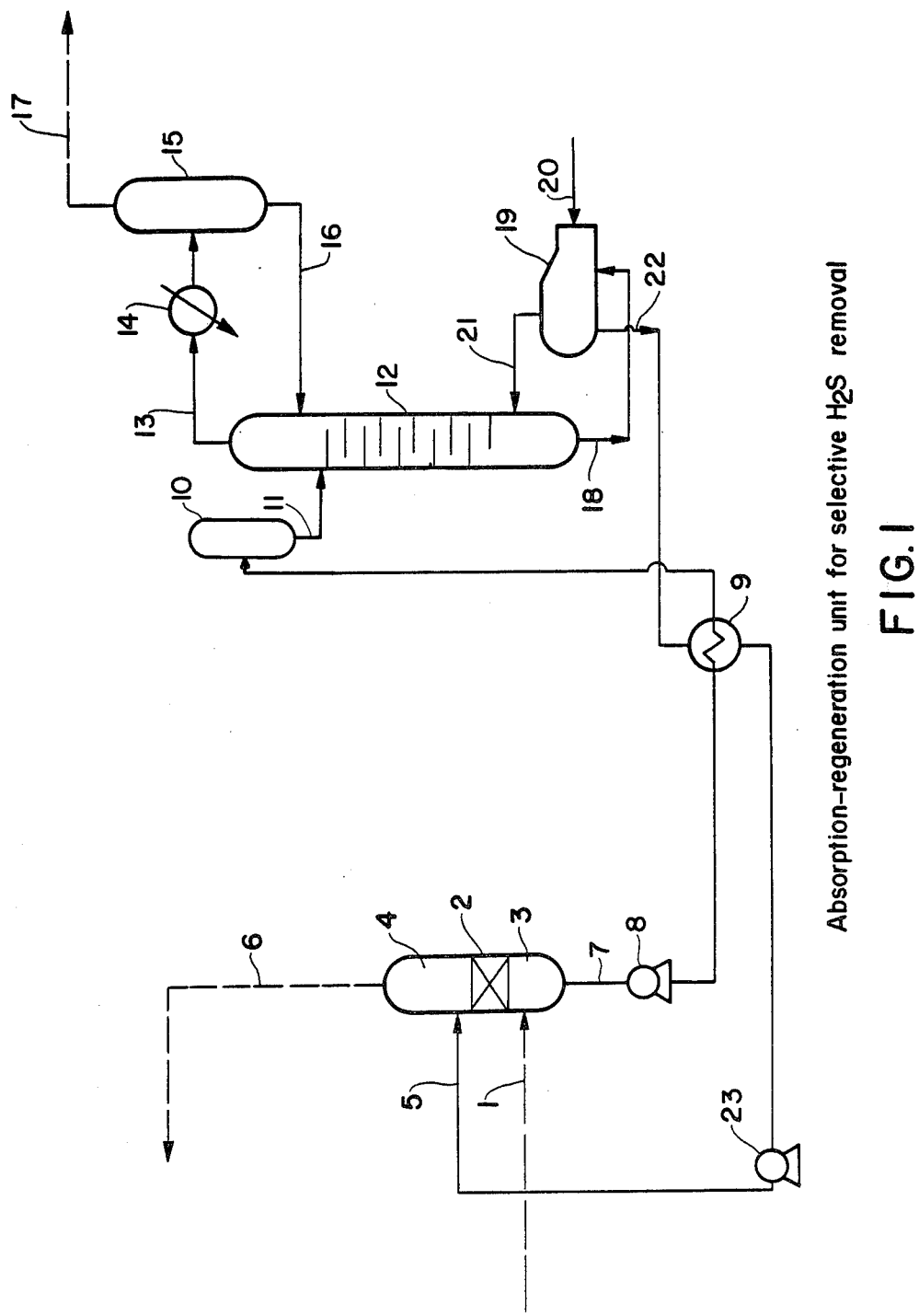
FIG. 1 is a diagrammatic flow sheet illustrating an absorption-regeneration unit for selective removal of $H_2S$ from gaseous streams containing $H_2S$ and $CO_2$.

The compounds of this invention are preferably represented by the following general formula:

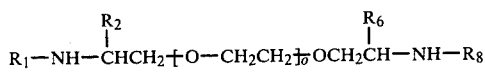

wherein $R_1$ and $R_8$ are each independently selected from the group consisting of secondary alkyl radicals having 3 to 8 carbon atoms and tertiary alkyl radicals having 4 to 8 carbon atoms, $R_2$ and $R_6$ are each independently selected from the group consisting of hydrogen and $C_1$-$C_3$ alkyl radicals, with the proviso that when $R_1$ and $R_8$ are secondary alkyl radicals, $R_2$ and $R_6$ are $C_1$-$C_3$ alkyl radicals, and o is either zero or a positive integer ranging from 1 to 4.

Typical compounds of the invention defined by the general formula above include:

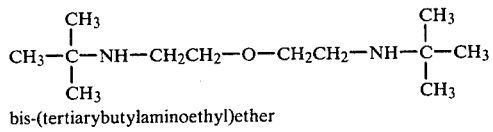
bis-(tertiarybutylaminoethyl)ether

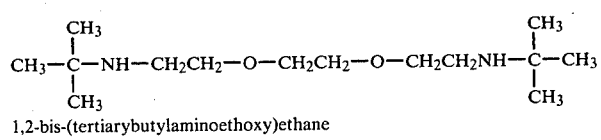
1,2-bis-(tertiarybutylaminoethoxy)ethane

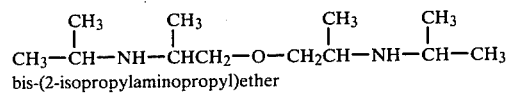
bis-(2-isopropylaminopropyl)ether

These novel bis-aminoethers may be prepared by reacting the appropriate primary amine, e.g., $R_1$—$NH_2$ and $R_8$—$NH_2$ with a bis-(haloalkoxy)alkane or bis-sulfonate ester of a glycolic ether under conditions such that the haloacid or sulfonic acid are eliminated. For example, 1,2-bis(t-butylaminoethoxy)ethane may be prepared by reacting t-butylamine with 1,2-(bis-chloroethoxy)ethane in a solvent such as ethylene glycol mono methylether under reflux conditions. The product can be simply recovered by treating the hot solution with an alkaline hydroxide followed by filtration and distillation of the product.

The amino ether compounds used in the absorbent process described above have a p$K_a$ value at 20° C. greater than 8.6, preferably greater than about 9.5 and more preferably the p$K_a$ value of the amino compound will range between about 9.5 and about 10.6. If the p$K_a$ is less than 8.6 the reaction with H₂S is decreased, whereas if the p$K_a$ of the amino ether compound is much greater than about 10.6, an excessive amount of steam is required to regenerate the solution. Also, to insure operational efficiency with minimal losses of the amino compound, the amino compound should have a relatively low volatility. For example, the boiling point of the amine (at 760 mm) is typically greater than about 180° C., preferably greater than 200° C., and more preferably greater than 225° C.

Three characteristics which are of ultimate importance in determining the effectiveness of the amino compounds herein for H₂S removal are "selectivity", "loading" and "capacity". The term "selectivity" as used throughout the specification is defined as the following mole ratio fraction:

$$\frac{\text{(moles of H}_2\text{S/moles of CO}_2\text{) in liquid phase}}{\text{(moles of H}_2\text{S/moles of CO}_2\text{) in gaseous phase}}$$

The higher this fraction, the greater the selectivity of the absorbent solution for the H₂S in the gas mixture.

By the term "loading" is meant the concentration of the H₂S and CO₂ gases physically dissolved and chemically combined in the absorbent solution as expressed in moles of gas per moles of the amine. The best amino compounds are those which exhibit good selectivity up to a relatively high loading level. The amino compounds used in the practice of the present invention typically have a "selectivity" of not substantially less than 10 at a "loading" of 0.1 moles, preferably, a "selectivity" of not substantially less than 10 at a loading of 0.2 or more moles of H₂S and CO₂ per moles of the amino compound.

"Capacity" is defined as the moles of H₂S loaded in the absorbent solution at absorption conditions less the moles of H₂S loaded in the absorbent solution at desorption conditions. High capacity enables one to reduce the amount of amine solution to be circulated and use less heat or steam during regeneration.

The acid gas mixture herein necessarily includes H₂S, and may optionally include other gases such as CO₂, N₂, CH₄, H₂, CO, H₂O, COS, HCN, C₂H₄, NH₃, and the like. Often such gas mixtures are found in combustion gases, refinery gases, town gas, natural gas, sun gas, water gas, propane, propylene, etc. The absorbent solution herein is particularly effective when the gaseous mixture is a low-Joule gas, obtained, for example, from shale oil retort gas, coal or gasification of heavy oil (POX), thermal conversion of heavy residual oil to lower molecular weight liquids and gases, or in sulfur plant tail gas clean-up operations.

The absorption step of this invention generally involves contacting the normally gaseous stream with the absorbent solution in any suitable contacting vessel. In such processes, the normally gaseous mixture containing H₂S and CO₂ from which the H₂S is to be selectively removed may be brought into intimate contact with the absorbent solution using conventional means, such as a tower or vessel packed with, for example, rings or with sieve plates, or a bubble reactor.

In a typical mode of practicing the invention, the absorption step is conducted by feeding the normally gaseous mixture into the lower portion of the absorption tower while fresh absorbent solution is fed into the upper region of the tower. The normally gaseous mixture, freed largely from the $H_2S$, emerges from the upper portion of the tower, and the loaded absorbent solution, which contains the selectively absorbed $H_2S$, leaves the tower near or at its bottom. Preferably, the inlet temperature of the absorbent solution during the absorption step is in the range of from about 20° to about 100° C., and more preferably from 40° to about 60° C. Pressures may vary widely; acceptable pressures are between 5 and 2000 psia, preferably 20 to 1500 psia, and most preferably 25 to 1000 psia in the absorber. The contacting takes place under conditions such that the $H_2S$ is selectively absorbed by the solution. The absorption conditions and apparatus are designed so as to minimize the residence time of the liquid in the absorber to reduce $CO_2$ pickup while at the same time maintaining sufficient residence time of gas mixture with liquid to absorb a maximum amount of the $H_2S$ gas. The amount of liquid required to be circulated to obtain a given degree of $H_2S$ removal will depend on the chemical structure and basicity of the amino compound and on the partial pressure of $H_2S$ in the feed gas. Gas mixtures with low partial pressures such as those encountered in thermal conversion processes will require more liquid under the same absorption conditions than gases with higher partial pressures such as shale oil retort gases.

A typical procedure for the selective $H_2S$ removal phase of the process comprises selectively absorbing $H_2S$ via countercurrent contact of the normally gaseous mixture containing $H_2S$ and $CO_2$ with the aqueous solution of the amino compound in a column containing a plurality of trays at a low temperature, e.g., below 45° C., and at a gas velocity of at least about 0.3 ft/sec (based on "active" or aerated tray surface), depending on the operating pressure of the gas, said tray column having fewer than 20 contacting trays, with, e.g., 4–16 trays being typically employed.

After contacting the normally gaseous mixture with the absorbent solution, which becomes saturated or partially saturated with $H_2S$, the solution may be at least partially regenerated so that it may be recycled back to the absorber. As with absorption, the regeneration may take place in a single liquid phase. Regeneration or desorption of the acid gases from the absorbent solution may be accomplished by conventional means such as pressure reduction of the solution or increase of temperature to a point at which the absorbed $H_2S$ flashes off, or by passing the solution into a vessel of similar construction to that used in the absorption step, at the upper portion of the vessel, and passing an inert gas such as air or nitrogen or preferably steam upwardly through the vessel. The temperature of the solution during the regeneration step should be in the range from about 50° to about 170° C., and preferably from about 80° to 120° C., and the pressure of the solution on regeneration should range from about 0.5 to about 100 psia, preferably 1 to about 50 psia. The absorbent solution, after being cleansed of at least a portion of the $H_2S$ gas, may be recycled back to the absorbing vessel. Makeup absorbent may be added as needed.

In the preferred regeneration technique, the $H_2S$-rich solution is sent to the regenerator wherein the absorbed components are stripped by the steam which is generated by re-boiling the solution. Pressure in the flash drum and stripper is usually 1 to about 50 psia, preferably 15 to about 30 psia, and the temperature is typically in the range from about 50° to 170° C., preferably about 80° to 120° C. Stripper and flash temperatures will, of course, depend on stripper pressure, thus at about 15 to 30 psia stripper pressures, the temperature will be about 80° to about 120° C. during desorption. Heating of the solution to be regenerated may very suitably be effected by means of indirect heating with low-pressure steam. It is also possible, however, to use direct injection of steam.

In one embodiment for practicing the entire process herein, as illustrated in FIG. 1, the gas mixture to be purified is introduced through line 1 into the lower portion of a gas-liquid countercurrent contacting column 2, said contacting column having a lower section 3 and an upper section 4. The upper and lower sections may be segregated by one or a plurality of packed beds as desired. The absorbent solution as described above is introduced into the upper portion of the column through a pipe 5. The solution flowing to the bottom of the column encounters the gas flowing countercurrently and dissolves the $H_2S$ preferentially. The gas freed from most of the $H_2S$ exits through a pipe 6 for final use. The solution, containing mainly $H_2S$ and some $CO_2$, flows toward the bottom portion of the column, from which it is discharged through pipe 7. The solution is then pumped via optional pump 8 through an optional heat exchanger and cooler 9 disposed in pipe 7, which allows the hot solution from the regenerator 12 to exchange heat with the cooler solution from the absorber column 2 for energy conservation. The solution is entered via pipe 7 to a flash drum 10 equipped with a line (not shown) which vents to line 13 and then introduced by pipe 11 into the upper portion of the regenerator 12, which is equipped with several plates and effects the desorption of the $H_2S$ and $CO_2$ gases carried along in the solution. This acid gas mixture is passed through a pipe 13 into a condenser 14 wherein cooling and condensation of water and amine solution from the gas occur. The gas then enters a separator 15 where further condensation is effected. The condensed solution is returned through pipe 16 to the upper portion of the regenerator 12. The gas remaining from the condensation, which contains $H_2S$ and some $CO_2$, is removed through pipe 17 for final disposal (e.g., to a vent or incinerator or an apparatus which converts the $H_2S$ to sulfur, such as a Claus unit or a Stretford conversion unit (not shown)).

The solution is liberated from most of the gas which it contains while flowing downward through the regenerator 12 and exits through pipe 18 at the bottom of the regenerator for transfer to a reboiler 19. Reboiler 19, equipped with an external source of heat (e.g., steam injected through pipe 20 and the condensate exits through a second pipe (not shown)), vaporizes a portion of this solution (mainly water) to drive further $H_2S$ therefrom. The $H_2S$ and steam driven off are returned via pipe 21 to the lower section of the regenerator 12 and exited through pipe 13 for entry into the condensation stages of gas treatment. The solution remaining in the reboiler 19 is drawn through pipe 22, cooled in heat exchanger 9, and introduced via the action of pump 23 (optional if pressure is sufficiently high) through pipe 5 into the absorber column 2.

The amino ether compounds herein are found to be superior to those used in the past, particularly to MDEA and DEAE, in terms of both selectivity and capacity for maintaining selectivity over a broad loading range. Typically, a gaseous stream to be treated having a 1:10 mole ratio of $H_2S:CO_2$ from an apparatus for thermal conversion of heavy residual oil, or a Lurgi coal gas having a mole ratio of $H_2S:CO_2$ of less than 1:10 will yield an acid gas having a mole ratio of $H_2S:CO_2$ of about 1:1 after treatment by the process of the present invention. The process herein may be used in conjunction with another $H_2S$ selective removal process; however, it is preferred to carry out the process of this invention by itself, since the amino compounds are extremely effective by themselves in preferential absorption of $H_2S$.

The invention is illustrated further by the following examples, which, however, are not to be taken as limiting in any respect. All parts and percentages, unless expressly stated to be otherwise, are by weight.

EXAMPLE 1

Preparation of 1,2-bis-(t-butylaminoethoxy)ethane

A solution of 2.5 moles of t-butylamine and 0.5 moles of 1,2-(bis-chloroethoxy)ethane in 600 ml of ethylene glycol mono methylether was refluxed for three days. Potassium hydroxide, 1.2 moles, was added, portionwise, to the hot solution and refluxing was continued for one hour. The cooled reaction was filtered, the solvent stripped, and the residue distilled. The recovered distillate had a b.p. of 104°–107° (0.25 mm), and the yield was 75%.

The product characterized by $^1H$ nmr showed signals at $\delta1.1$ (s, 18H); $\delta2.74$ (t,4H); $\delta3.6$ (t,8H). Analysis calculated for $C_{14}H_{32}N_2O_2$: %N, 10.77: Found: %N, 10.34.

EXAMPLE 2

Selective $H_2S$ removal from a mixture containing $H_2S$ and $CO_2$

Figure 2:
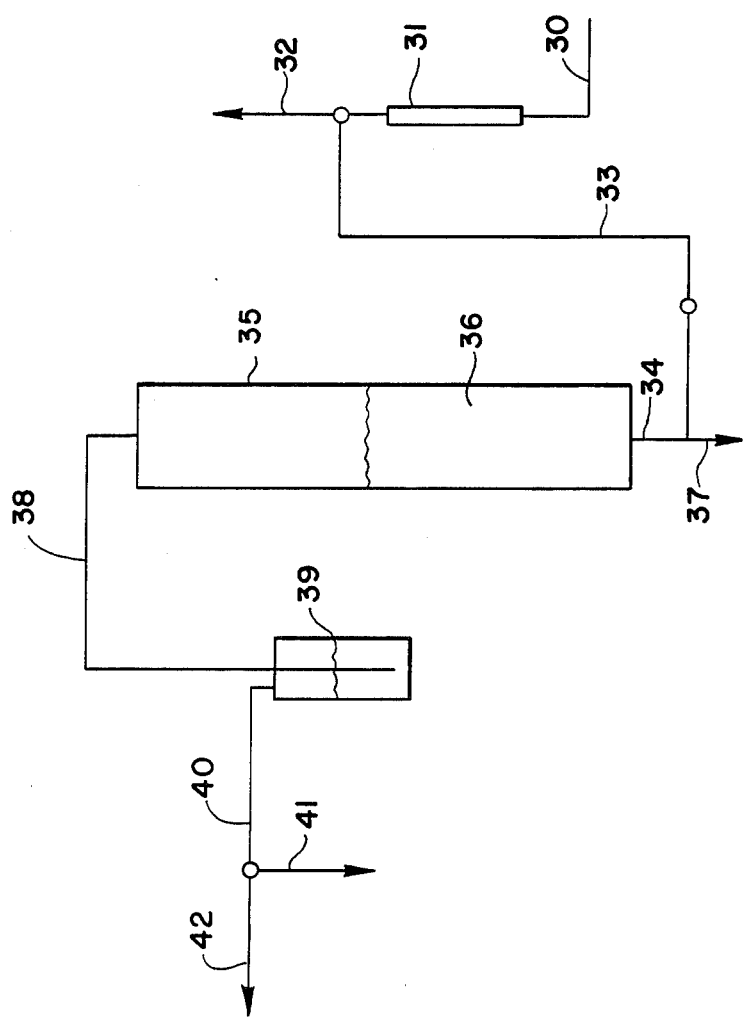
FIG. 2 is a diagrammatic flow sheet illustrating an experimental sparged absorber unit for use in rapid determination of the selectivity of the amino compound for selective removal of H₂S from gaseous streams containing H2S and CO2.

FIG. 2 illustrates the sparged absorber unit, operated on a semi-batch mode, used to evaluate the selectivity for $H_2S$ removal of the amino compounds of the invention herein. A gas mixture comprised of 10% $CO_2$, 1% $H_2S$ and 89% $N_2$, expressed in volume percent, respectively, was passed from a gas cylinder (not shown) through line 30 to a meter 31 measuring the rate at which the gas is fed to the absorber. For all examples this rate was 3.6 liters per minute. The gas was then passed through line 32 to a gas chromatography column (not shown) continuously monitoring the composition of the inlet gas and through lines 33 and 34 to a sparged absorber unit 35, which is a cylindrical glass tube 45 cm high and 3.1 cm in diameter charged with 100 ml of the absorbent amine solution 36. The gas was passed through the solution at a solution temperature of 40° C., and 10-ml samples of the solution were periodically removed from the bottom of the absorber unit through lines 34 and 37 to be analyzed for $H_2S$ and $CO_2$ content. The $H_2S$ content in the liquid sample was determined by titration with silver nitrate. The $CO_2$ content of the liquid sample was analyzed by acidifying the sample with an aqueous solution of 10% HCl and measuring the evolved $CO_2$ by weight gain on NaOH-coated asbestos.

While the solution was being periodically withdrawn from the bottom of the absorber unit, the gas mixture was removed from the top thereof via line 38 to a trap 39 which served to scrub out any $H_2S$ in the outlet gas. The resulting gas could optionally then be passed via lines 40 and 41 for final disposal or via line 42 to a gas chromatography column (not shown) for periodic evaluation of the composition of the outlet gas to check for system leaks. For purposes of the examples, the $H_2S$ and $CO_2$ contents of the inlet gas phase were measured, and the $H_2S$ and $CO_2$ contents of the liquid phase were determined as described above. These data were used to calculate selectivity values of the amine as defined above, which were plotted as a function of the loading of the absorbent solution with $H_2S$ and $CO_2$, in units of moles acid gas per moles of the amino compound.

In this example an aqueous 1.5M solution of 1,2-bis-(tertiarybutylaminoethoxy)ethane (BIS-TB) was employed as the absorbent solution. The selectivity data of BIS-TB were plotted and are shown in FIG. 3.

EXAMPLE 3

The procedure of Example 2 was repeated using as the absorbent solution a 3 molar aqueous solution of t-butylaminoethoxyethanol (TBEE) and the selectivity data were plotted on the graph as shown in FIG. 3.

EXAMPLE 4

The procedure of Example 2 was repeated using as the absorbent solution a 1.5M aqueous solution of 1,2-bis-(isopropylaminoethoxy)ethane (BIS-IP) and the selectivity data were plotted on the graph as shown in FIG. 3.

EXAMPLE 5

The procedure of Example 2 was repeated using as the absorbent solution a 3M aqueous solution of methyldiethanolamine (MDEA) and the selectivity data were plotted on the graph as shown in FIG. 3.

The results shown in FIG. 3 indicate that the severely sterically hindered bis-secondary aminoethers of the present invention are far superior to the bis-secondary aminoethers that are not severely hindered or the tertiary amine, MDEA.

While all examples herein illustrate the superior performance of the amino compounds for selective $H_2S$ removal using an absorber unit as represented by FIG. 2, it will also be possible to achieve effective selective $H_2S$ removal by using the amino compounds in an absorption-regeneration unit as depicted in FIG. 1.

In summary, this invention is seen to provide a special class of amino compounds characterized as bis-(secondary and tertiary alkylaminoalkoxy)alkanes having a high selectivity for $H_2S$ in preference to $CO_2$ which selectivity is maintained at high $H_2S$ and $CO_2$ loading levels.

These amino compounds are capable of reducing the $H_2S$ in gaseous mixtures to a relatively low level, e.g., less than about 200 Vppm and have a relatively high capacity for $H_2S$, e.g., greater than about 0.2 mole of $H_2S$ per mole of amine. The amino compounds are characterized as having a "kinetic selectivity" for $H_2S$, i.e., a faster reaction rate for $H_2S$ than for $CO_2$ at absorption conditions. In addition they have a higher capacity for $H_2S$ at equivalent kinetic selectivity for $H_2S$ over $CO_2$. This higher capacity results in the economic advantage of lower steam requirements during regeneration.

The data in FIG. 3 also show that the amino compounds of the present invention have very high capacity for both $H_2S$ and $CO_2$ compared to methyldiethanolamine (MDEA) in addition to high $H_2S$ selectivities. It will be apparent from an inspection of the data in FIG. 3 that if the absorption process is conducted under conditions such that the amino compound has a long contact time with the gases to be absorbed, the selectivity for $H_2S$ decreases, but the overall capacity for both $CO_2$ and $H_2S$ remains rather high. Therefore, one may, in some instances, wish to carry out a "non-selective" absorption process to take advantage of the large absorption capacity of the amino compounds of the invention. Accordingly, one may carry out a "non-selective" acid gas removal absorption process using the amino compounds of the invention. Such "non-selective" processes are particularly useful in scrubbing natural gases which contain relatively high levels of $H_2S$ and low to nil levels of $CO_2$. As such, the amino compounds of the invention may replace some or all of monoethanolamine (MEA) or diethanolamine (DEA) commonly used for such scrubbing processes.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A di-secondary aminoether of the general formula:

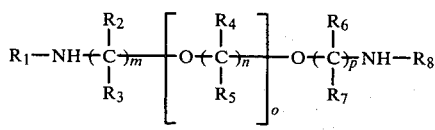

wherein $R_1$ and $R_8$ are each independently selected from the group consisting of primary alkyl having 1 to 8 carbon atoms and primary hydroxyalkyl radicals having 2 to 8 carbon atoms, secondary alkyl and secondary hydroxyalkyl having 3 to 8 carbon atoms, tertiary alkyl and tertiary hydroxyalkyl, cycloalkyl and hydroxycycloalkyl radicals having 3 to 8 carbon atoms, $R_2$, $R_3$, $R_4$, $R_5$, $R_6$ and $R_7$ are each independently selected from the group consisting of hydrogen, $C_1$–$C_4$ alkyl and hydroxyalkyl radicals, with the proviso that $R_2$, $R_3$, $R_6$ and $R_7$ bonded to the carbon atoms directly bonded to the nitrogen atoms are $C_1$–$C_4$ alkyl or hydroxyalkyl radicals when $R_1$ and $R_8$ are primary alkyl or primary hydroxyalkyl radicals and that at least one of $R_2$ or $R_3$ and $R_6$ or $R_7$ bonded to the carbon atoms directly bonded to the nitrogen atoms are $C_1$ to $C_4$ alkyl or hydroxyalkyl radicals when $R_1$ and $R_8$ are secondary alkyl, secondary hydroxyalkyl, or cycloalkyl or hydroxycycloalkyl radicals, m, n and p are positive integers ranging from 2 to 4, and o is either zero or a positive integer ranging from 1 to 10.

2. The aminoether of claim 1 wherein $R_1$ and $R_8$ are selected from the group consisting of tertiary-butyl, tertiary-amyl, cyclopentyl, cyclohexyl, and isopropyl radicals.

3. The aminoether of claim 2 wherein $R_1$ and $R_8$ are each a tertiary-butyl radical and $R_2$, $R_3$, $R_4$, $R_5$, $R_6$ and $R_7$ are each hydrogen.

4. The aminoether of claims 1, 2 or 3 wherein the symbols m, n and p are 2 and the symbol o is 0 or 1.

5. A di-secondary aminoether of the general formula:

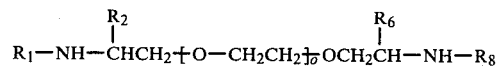

wherein $R_1$ and $R_8$ are each independently selected from the group consisting of secondary alkyl radicals having 3 to 8 carbon atoms, and tertiary alkyl radicals having 4 to 8 carbon atoms, $R_2$ and $R_6$ are each independently selected from the group consisting of hydrogen and $C_1$–$C_3$ alkyl radicals, with the proviso that when $R_1$ and $R_8$ are secondary alkyl radicals, $R_2$ and $R_6$ are $C_1$–$C_3$ alkyl radicals, and o is either zero or a positive integer ranging from 1 to 4.

6. The aminoether of claim 5 wherein $R_1$ and $R_8$ are each isopropyl radicals and $R_2$ and $R_6$ are each methyl radicals.

7. The aminoether of claim 5 or 6 wherein the symbol o is zero or 1.

8. A bis-secondary aminoether of the formula:

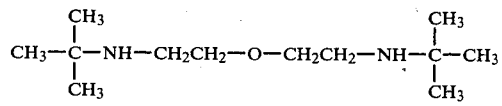

9. A di-secondary aminoether of the formula:

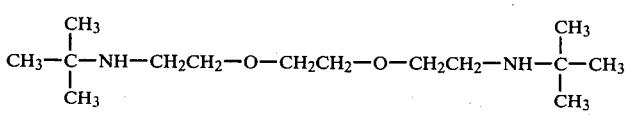

10. A bis-secondary aminoether of the formula:

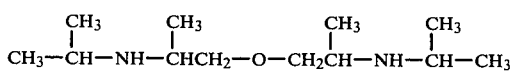

11. A di-secondary aminoether of the formula:

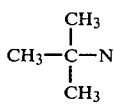

12. A blend composition comprising a disecondary aminoether of claim 1 and another amino compound.

13. The blend of claim 12 wherein the other amino compound is methyldiethanolamine.

* * * * *